(12) United States Patent
Morita et al.

(10) Patent No.: US 8,956,307 B2
(45) Date of Patent: Feb. 17, 2015

(54) BLOOD COLLECTION SET, SAMPLING HOLDER, AND NEEDLESTICK-PREVENTIVE NEEDLE COVER

(75) Inventors: Masayuki Morita, Saiki (JP); Masatoshi Watanabe, Saiki (JP); Takenori Sakura, Saiki (JP)

(73) Assignee: Kawasumi Laboratories, Inc., Oita (JP)

(*) Notice: Subject to any disclaimer, the term of this patent is extended or adjusted under 35 U.S.C. 154(b) by 328 days.

(21) Appl. No.: 13/380,277

(22) PCT Filed: Jun. 28, 2010

(86) PCT No.: PCT/JP2010/061001
§ 371 (c)(1),
(2), (4) Date: Dec. 22, 2011

(87) PCT Pub. No.: WO2011/001950
PCT Pub. Date: Jan. 6, 2011

(65) Prior Publication Data
US 2012/0095368 A1    Apr. 19, 2012

(30) Foreign Application Priority Data
Jul. 1, 2009   (JP) .................. 2009-156592

(51) Int. Cl.
*A61B 5/00*   (2006.01)
*B65D 81/00*  (2006.01)
(Continued)

(52) U.S. Cl.
CPC .......... *A61B 5/1438* (2013.01); *A61B 5/15003* (2013.01); *A61B 5/150389* (2013.01);
(Continued)

(58) Field of Classification Search
CPC ........................................... A61B 5/00
USPC .................. 600/573, 575, 580, 576, 577
See application file for complete search history.

(56) References Cited

U.S. PATENT DOCUMENTS 4,784,650 A * 11/1988 Coburn .................. 604/272
4,790,827 A * 12/1988 Haber et al. ............ 604/198
(Continued)

FOREIGN PATENT DOCUMENTS

JP   2002-521146 A   7/2002
JP   2004-194728 A   7/2004
(Continued)

OTHER PUBLICATIONS

Office Action dated Dec. 24, 2012 issued by the Taiwanese Patent Office in corresponding Taiwanese Application No. 099121644.
(Continued)

*Primary Examiner* — Rene Towa
*Assistant Examiner* — May Abouelela
(74) *Attorney, Agent, or Firm* — Sughrue Mion, PLLC (57) ABSTRACT

An object is to provide a blood collection set configured such that a sampling holder and a needlestick-preventive needle cover are more difficult to disengage from each other than conventional. A blood collection set (500) includes a sampling holder (100) and a needlestick-preventive needle cover (200). The sampling holder (100) includes a tubular body (110), a lid (130), and a fitting portion (140) having a circumferential rib as a rib portion and a catching portion. The needlestick-preventive needle cover (200) includes an engaging portion (250) that is engageable with the catching portion of the sampling holder (100).

6 Claims, 7 Drawing Sheets (51) Int. Cl.
  *A61B 5/15* (2006.01)
  *A61B 5/151* (2006.01)
  *A61B 5/153* (2006.01)
  *A61B 5/154* (2006.01)
  *A61M 1/02* (2006.01)

(52) U.S. Cl.
  CPC ..... *A61B5/150503* (2013.01); *A61B 5/150572* (2013.01); *A61B 5/150595* (2013.01); *A61B 5/150633* (2013.01); *A61B 5/150732* (2013.01); *A61B 5/150992* (2013.01); *A61B 5/15105* (2013.01); *A61B 5/153* (2013.01); *A61B 5/154* (2013.01); *A61M 1/0209* (2013.01); *A61M 1/0218* (2014.02); *A61M 1/0236* (2014.02)
  USPC .......... 600/573; 600/575; 600/576; 600/577; 600/580

(56) References Cited

U.S. PATENT DOCUMENTS

| | | | | |
|---|---|---|---|---|
| 4,805,635 | A * | 2/1989 | Korf et al. | 600/576 |
| 4,840,618 | A * | 6/1989 | Marvel | 604/187 |
| 4,932,418 | A * | 6/1990 | Coburn | 600/577 |
| 5,120,311 | A * | 6/1992 | Sagstetter et al. | 604/110 |
| 5,267,977 | A * | 12/1993 | Feeney, Jr. | 604/198 |
| 5,423,758 | A * | 6/1995 | Shaw | 604/110 |
| 5,423,765 | A * | 6/1995 | Hollister | 604/192 |
| 5,514,100 | A * | 5/1996 | Mahurkar | 604/195 |
| 5,682,664 | A | 11/1997 | Joyce | |
| 5,687,740 | A * | 11/1997 | Sheridan | 600/573 |
| 5,752,936 | A * | 5/1998 | Chen | 604/110 |
| 5,769,826 | A * | 6/1998 | Johnson et al. | 604/195 |
| 5,782,820 | A * | 7/1998 | Roland | 604/411 |
| 5,938,644 | A * | 8/1999 | Kirk | 604/263 |
| 6,030,582 | A * | 2/2000 | Levy | 422/570 |
| 6,416,497 | B1 * | 7/2002 | Kirk | 604/198 |
| 6,540,696 | B1 * | 4/2003 | Dillon et al. | 600/573 |
| 6,595,931 | B2 * | 7/2003 | Ranford | 600/573 |
| 6,648,835 | B1 * | 11/2003 | Shemesh | 600/573 |
| D484,242 | S * | 12/2003 | Wilkinson | D24/130 |
| RE39,107 | E * | 5/2006 | Shaw | 604/110 |
| 7,396,342 | B2 * | 7/2008 | Wang et al. | 604/110 |
| 7,479,131 | B2 * | 1/2009 | Mathias et al. | 604/409 |
| 7,521,022 | B2 * | 4/2009 | Konrad | 422/550 |
| 8,052,653 | B2 * | 11/2011 | Gratwohl et al. | 604/198 |
| 8,167,820 | B2 * | 5/2012 | Mahurkar | 600/577 |
| 8,632,503 | B2 * | 1/2014 | Ruan et al. | 604/198 |
| 2004/0082898 | A1 | 4/2004 | Mathias et al. | |
| 2004/0082899 | A1 * | 4/2004 | Mathias et al. | 604/6.16 |
| 2006/0089566 | A1 * | 4/2006 | DeHart | 600/573 |
| 2007/0123821 | A1 * | 5/2007 | Wang et al. | 604/110 |
| 2009/0259196 | A1 * | 10/2009 | Gratwohl et al. | 604/198 |
| 2010/0174182 | A1 * | 7/2010 | Costanzo | 600/431 |
| 2010/0241029 | A1 * | 9/2010 | Mahurkar | 600/577 |
| 2011/0288441 | A1 * | 11/2011 | Taguchi | 600/580 |

FOREIGN PATENT DOCUMENTS

| | | |
|---|---|---|
| JP | 2005-230232 A | 9/2005 |
| JP | 3123813 U | 7/2006 |
| JP | 3137417 U | 11/2007 |

OTHER PUBLICATIONS

International Search Report (PCT/ISA/210) issued by the International Searching Authority in corresponding International Application No. PCT/JP2010/061001 on Jul. 20, 2010.

Notification of Receipt of Search Copy (PCT/ISA/202) issued by the International Searching Authority in corresponding International Application No. PCT/JP2010/061001 on Jul. 6, 2010.

Written Opinion (PCT/ISA/237) of the International Searching Authority in corresponding International Application No. PCT/JP2010/061001 on Jul. 20, 2010.

* cited by examiner

BLOOD COLLECTION SET, SAMPLING HOLDER, AND NEEDLESTICK-PREVENTIVE NEEDLE COVER

TECHNICAL FIELD

The present invention relates to a blood collection set, a sampling holder, and a needlestick-preventive needle cover.

BACKGROUND ART

Conventionally, a blood collection set having a blood collection needle, a blood bag, a sampling holder, and a needlestick-preventive needle cover is known (see, e.g., Patent Document 1).

The conventional sampling holder described in Patent Document 1 has a substantially cylindrical body, and a lid (a cap) which is attached to or detached from the body. This lid is provided with a fitting portion (an inner cylinder of the cap). After a blood collection, a blood collection needle to be discarded is accommodated in a needlestick-preventive needle cover. Then, the needlestick-preventive needle cover is pushed into the fitting portion of the lid, and the sampling holder and the needlestick-preventive needle cover are discarded together with the blood collection needle. Accordingly, the blood collection needle can be prevented from being exposed when discarding the sampling holder and the needlestick-preventive needle. As a result, it is possible to reduce the risk of needlestick and blood infection that may occur when discarding with the blood collection needle being exposed.

PRIOR ART DOCUMENT

Patent Document

Patent Document 1: JP 3123813 U

SUMMARY OF THE INVENTION

Problems to be Solved by the Invention

In a place where a blood collection set is used, such as blood donation, from a safety point of view, the risk of needlestick and blood infection occurring at the time of disposal of the blood collection is desired to be as close as possible to zero. Thus, a blood collection set is desired to have a sampling holder and a needlestick-preventive needle cover that are more difficult to disengage from each other.

To prevent the sampling holder and the needlestick-preventive needle cover of from disengaging from each other to address such a demand with the conventional blood collection set described in Patent Document 1, the needlestick-preventive needle cover needs to be pushed into the fitting portion of the lid by a relatively strong force. It is of course important to enhance secure engagement of the sampling holder and the needlestick-preventive needle cover. However, it is desired from the viewpoint of a user of the blood collection set that the needlestick-preventive needle cover can be fit into the fitting portion by a smaller force.

The present invention has been made in view of such a demand, and it is an object thereof to provide a blood collection set, a sampling holder, and a needlestick-preventive needle cover, in which the sampling holder and the needlestick-preventive needle cover more difficult to disengage from each other than conventional, and the needlestick-preventive needle cover can be fit into a fitting portion of the sampling holder with a smaller force than conventional.

Means for Solving the Problems

[1] A blood collection set (500) according to the present invention includes:
a sampling holder (100) having a tubular body (110) with an opening portion (111), a lid (130) configured to open and close the opening portion (111) of the tubular body (110), and a fitting portion (140) provided on a surface of the lid (130) on a side opposite to the tubular body (110), and
a needlestick-preventive needle cover (200) configured to fit into the fitting portion (140), in which
the fitting portion (140) includes:
a rib portion (141); and
a catching portion (142) having one or more protrusions or recesses provided on the rib portion (141), and
the needlestick-preventive needle cover (200) includes an engaging portion (250) configured to engage with the catching portion (142).

Thus, according to a blood collection set according to the present invention, when fitting the needlestick-preventive needle cover into the fitting portion, the catching portion catches the engaging portion. Accordingly, due to the engagement force of the catching portion and the engaging portion, the sampling holder and the needlestick-preventive needle cover are considerably more difficult to disengage from each other than conventional.

In addition, according to the blood collection set of the present invention, the needlestick-preventive needle cover is fit into the fitting portion of the sampling holder by engaging the catching portion with the engaging portion. Thus, the needlestick-preventive needle cover can be fit into the fitting portion of the lid by a smaller force, as compared with the case of the conventional blood collection set in which the needlestick-preventive needle cover is pressed into the fitting portion of the lid.

[2] It is preferable in the blood collection set (500) described in [1] that the catching portion (142) includes a plurality of protrusions or a plurality of recesses.

With this configuration, the blood collection set is such that the sampling holder and the needlestick-preventive needle cover become more difficult to disengage from each other.

[3] It is preferable in the blood collection set (500) described in [2] that the rib portion is a circumferential rib (141), and that the plurality of protrusions or the plurality of recesses are arranged symmetrically with respect to an imaginary line (L1) perpendicular to a central axis of the circumferential rib (141).

With this configuration, the protrusions or the recesses are arranged in a balanced manner. Thus, there is no imbalance of locations where the needlestick-preventive needle cover is caught. Accordingly, the blood collection set becomes such that the sampling holder and the needlestick-preventive needle cover are difficult to disengage from each other, and are easy to fit in.

[4] It is preferable in the blood collection set (500) described in any one of [1] to [3] that the catching portion (142) includes the protrusions, and that holes (143) are provided in a boundary portion between the rib portion (141) and the surface of the lid (130) on the side opposite to the tubular body (110) and at positions corresponding to the protrusions.

With this configuration, a backlash at the time of pushing the needlestick-preventive needle cover into the fitting portion can be reduced. Consequently, the resistance at the time of fitting the needlestick-preventive needle cover into the fitting portion can be reduced. Accordingly, the needlestick-preventive needle cover can be fit into the fitting portion with a smaller force.

[5] It is preferable in the blood collection set (500) described in any one of [1] to [4] that the catching portion (142) includes the protrusions, and that distal ends (142P) of the catching portion (142) extend toward a surface of the lid (130) on a side of the tubular body (110).

With this configuration, the catching portion serves as a so-called "barb", so that the engaging portion and the catching portion can be made more difficult to disengage from each other. Consequently, the blood collection set becomes such that the sampling holder and the needlestick-preventive needle cover are more difficult to disengage from each other.

[6] It is preferable in the blood collection set (500) described in any one of [1] to [5] that a click portion (131) is provided on an end portion of the lid (130), and that a click engaging portion (115) engaging with the click portion (131) is provided near the opening portion (111) of the tubular body (110).

With this configuration, the opening portion of the tubular body can easily be closed by the lid.

[7] A sampling holder (100) according to the present invention includes:
a tubular body (110) having an opening portion (111), a lid (130) configured to open and close the opening portion (111) of the tubular body (110), and a fitting portion (140) provided on a surface of the lid (130) on a side opposite to the tubular body (110), in which
the fitting portion (140) includes:
a rib portion (141); and
a catching portion (142) having one or more protrusions or recesses provided on the rib portion (141).

The sampling holder according to the present invention includes the catching portion. Thus, for a reason similar to that in the case of the blood collection set described in [1], the sampling holder is such that, when the needlestick-preventive needle cover is fit into the sampling holder, the needlestick-preventive needle cover is more difficult to disengage therefrom than conventional, and that the needlestick-preventive needle cover can be fit in with a smaller force than conventional.

[8] It is preferable in the sampling holder (100) described in [7] that the catching portion (142) includes a plurality of protrusions or a plurality of recesses.

With this configuration, the sampling holder is such that when the needlestick-preventive needle cover is fit into the sampling holder, the needlestick-preventive needle cover is more difficult to disengage therefrom.

[9] It is preferable in the sampling holder (100) described in [7] or [8] that the catching portion (142) includes the protrusions, and that holes (143) are provided in a boundary portion between the rib portion (141) and the surface of the lid (130) on the side opposite to the tubular body (110) and at positions corresponding to the protrusions.

With this configuration, for a reason similar to that in the case of the blood collection set described [4], the sampling holder becomes such that, when fitting the needlestick-preventive needle cover into the sampling holder, the needlestick-preventive needle cover can be fit in by a smaller force.

[10] A needlestick-preventive needle cover (200) according to the present invention includes an engaging portion (250) configured to engage with the catching portion (142) of the sampling holder (100) described in [7].

The needlestick-preventive needle cover according to the present invention includes the engaging portion. Thus, for a similar to that in the case of the blood collection set described in [1], the needlestick-preventive needle cover is such that when the needlestick-preventive needle cover is fit into the sampling holder, the needlestick-preventive needle cover is more difficult to disengage from the sampling holder than conventional, and that the needlestick-preventive needle cover can be fit into the fitting portion of the sampling holder by a smaller force than conventional.

The reference signs in parentheses added to the terms for respective parts or the like in this section (the section of Means of Solving the Problems) are used to facilitate the understanding of contents described in this section, and not to limit the contents described in this section.

Advantages of the Invention

With the blood collection set having the sampling holder and the needlestick-preventive needle cover according to the present invention, the sampling holder and the needlestick-preventive needle cover can securely engage with each other. Thus, the sampling holder and the needlestick-preventive needle cover are considerably more difficult to disengage from each other than conventional. Consequently, the risk needlestick and blood infection occurring at the time of disposal of the blood collection set can be further reduced, so that safety at the time of disposal can be further improved. In addition, because the needlestick-preventive needle cover is fit into the fitting portion of the sampling holder by engaging the catching portion and the engaging portion with each other, the needlestick-preventive needle cover can be fit into the fitting portion with a smaller force, as compared with the case of the conventional blood collection set in which the needlestick-preventive needle cover is pushed into the fitting portion of the lid.

BRIEF DESCRIPTION OF THE DRAWINGS

FIGS. 6(a) and 6(b) are views illustrating a fitting portion 140 of the sampling holder 100, in which

FIGS. 7(a) and 7(b) are views illustrating the fitting between the needlestick-preventive needle cover 200 and the sampling holder 100, in which

FIGS. 8(a) and 8(b) are views illustrating the relationship between each catching portion 142 and an associated engaging portion 250 at the fitting therebetween, in which

EMBODIMENTS OF THE INVENTION

Hereinafter, a blood collection set, a needlestick-preventive needle cover, and a sampling holder according to the invention are described, based on an embodiment illustrated in the drawings.

Embodiment

A blood collection set according to the invention includes at least a sampling holder and a needlestick-preventive needle cover.

Blood Collection Set 500

First, the configuration of a blood collection set 500 according to the embodiment is described with reference to FIG. 1.

Figure 1:
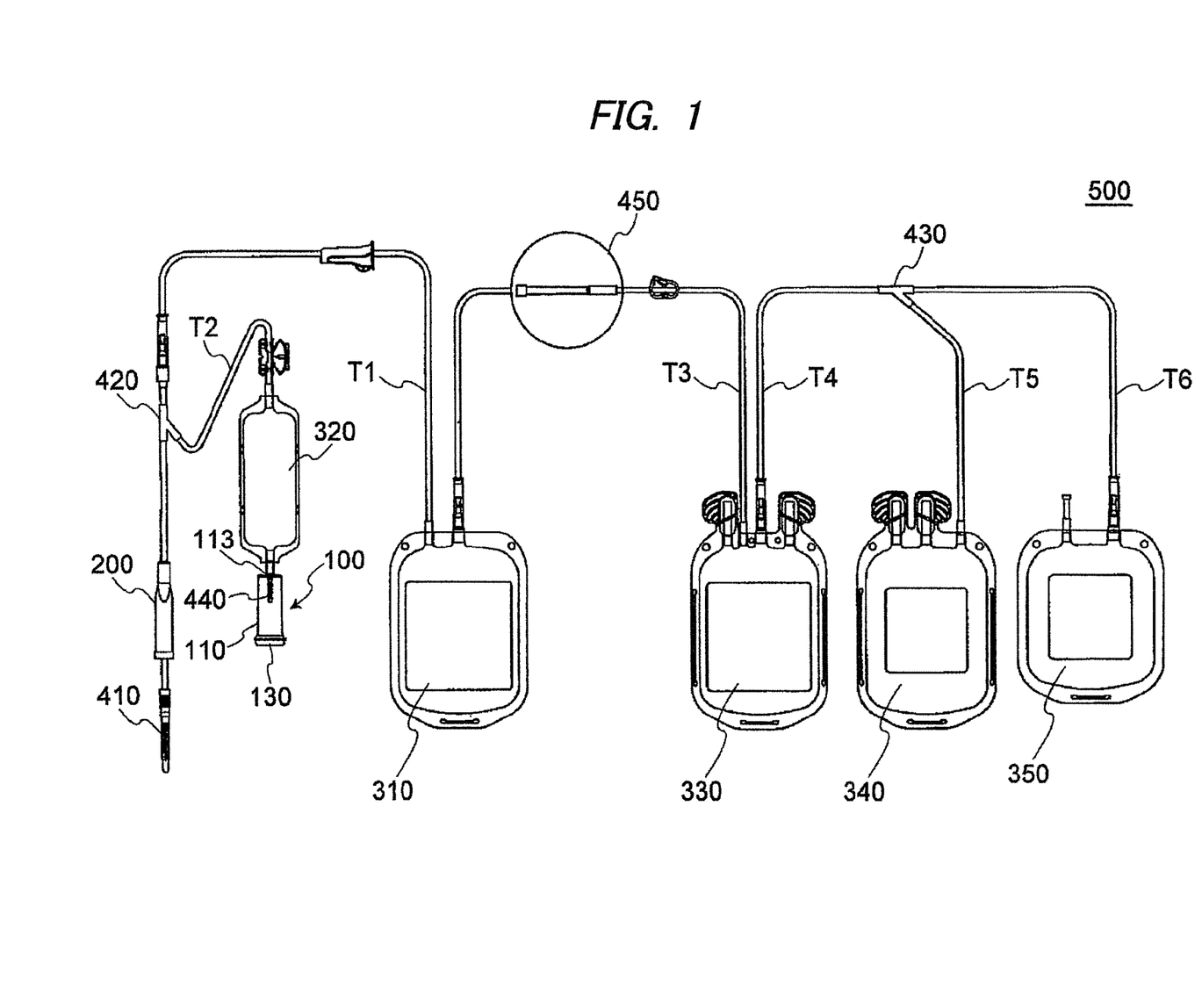
FIG. 1 is a view for describing a blood collection set 500 according to an embodiment.

FIG. 1 is a view for describing the blood collection set 500 according to the embodiment.

As illustrated in FIG. 1, the blood collection set 500 has a plurality of bags (a blood bag 310, a sampling bag 320, a first bag 330, a second bag 340, and a blood storage solution containing bag 350) for collecting or preserving blood and the like, a blood collection needle 410, a blood filter 450, a needlestick-preventive needle cover 200, and a sampling holder 100.

The blood bag 310 is connected to the blood collection needle 410 via a blood collection tube T1. A first branching tube 420 is provided at a partway position on the blood collection tube T1. A sampling bag 320 is connected to the branching tube 420 via an initial blood flow introduction tube T2. The sampling holder 100 is connected to the sampling bag 320. The needlestick-preventive needle cover 200 is attached to the blood collection tube T1 near the blood collection needle 410.

The blood bag 310 is connected to the first bag 330 via the first connection tube T3, in addition to the blood tube T1. The blood filter 450 aimed at removing leukocytes is provided at a partway position on the first connection tube T3. In addition to the first connection tube T3, the first bag 330 is connected to the second branching tube 430 via a second connection tube T4. One of branches of the second branching tube 430 is connected to the second bag 340 via a third connection tube T5, the other branch thereof is connected to the blood storage solution containing bag 350 via a fourth connection tube T6.

The blood bag 310 and the blood storage solution containing bag 350 accommodate blood storage solutions such as MAP (mannitol adenine phosphate) solutions or anticoagulants (not shown).

Needlestick-Preventive Needle Cover 200

Figure 2:
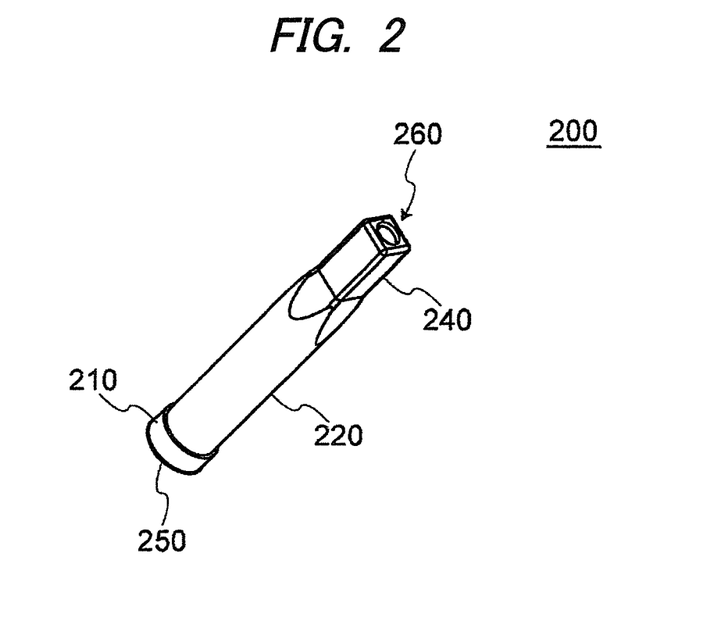
FIG. 2 is a perspective view of a needlestick-preventive needle cover 200.
Figure 3:
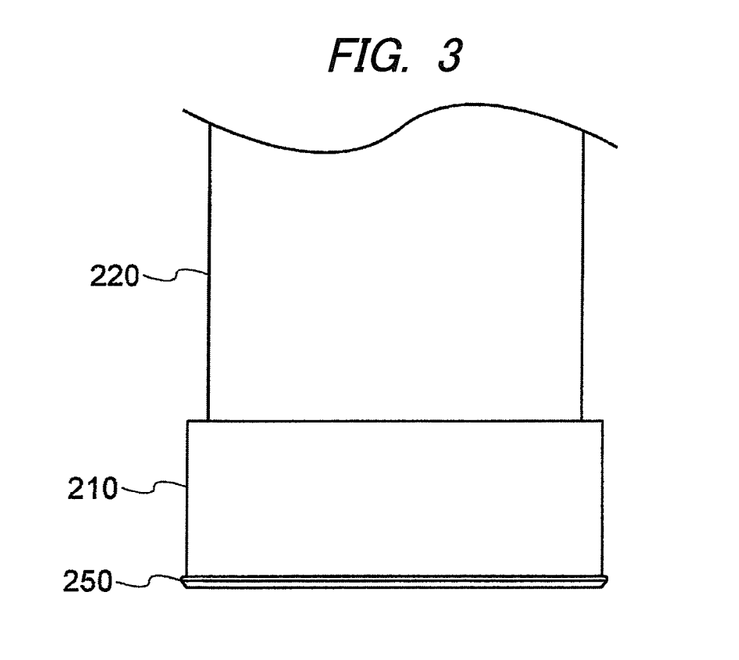
FIG. 3 is a partially enlarged view of an engaging portion 250 of the needlestick-preventive needle cover 200.

FIG. 2 is a perspective view of the needlestick-preventive needle cover 200. FIG. 3 is a partially enlarged view of the engaging portion 250 of the needlestick-preventive needle cover 200.

As illustrated in FIG. 2, the needlestick-preventive needle cover 200 according to the embodiment is configured by a tubular body opened at both ends. A tubular body flange portion 210, a large-diameter portion 220, and a polygonal portion 240 are formed to be arranged therein from one of the ends to the other end of the tubular body. In the description of the needlestick-preventive needle cover in the present specification, a side of the needlestick-preventive needle cover 200, which is close to the tubular body flange portion 210, is defined as a base end side thereof, while the other side thereof, which is close to the polygonal portion 240, is defined as a leading end side thereof.

As illustrated in FIGS. 2 and 3, the engaging portion 250 outwardly protruding over the entire circumference thereof is provided on the outer edge of an opening at the base end side of the needlestick-preventive needle cover 200. The engaging portion 250 has a tapered shape whose diameter decreases towards the base end side. On the other hand, an opening at the leading end side of the needlestick-preventive needle cover 200 is a tube insertion path 260, so that the diameter of the opening is slightly larger than that of the blood collection tube T1.

The tubular body flange portion 210 has a circular cross-section whose outside diameter has a value set so that the tubular body flange portion 210 is placed within the inner circumferential surface of a fitting portion 140 provided in a lid 130 of the sampling holder 100, which will be described below.

The large-diameter portion 220 also has a circular cross-section. The outside diameter of the large-diameter portion 220 is slightly smaller than that of the tubular body flange portion 210. However, the large-diameter portion 220 is formed such that the inside diameter thereof is substantially equal to that of the tubular body flange portion 210.

The polygonal portion 240 has a substantially square cross-section.

Incidentally, plastic materials, such as polypropylene, can preferably be used as the material of the needlestick-preventive needle cover 200.

As illustrated in FIG. 1, the needlestick-preventive needle cover 200 is installed by being inserted into the blood collection tube T1 while directing the base end thereof towards the blood collection needle 410. After the blood collection, the needlestick-preventive needle cover 200 is slid towards the blood collection needle 410 to accommodate the blood collection needle 410 in the needlestick-preventive needle cover 200.

Sampling Holder 100

Figure 4:
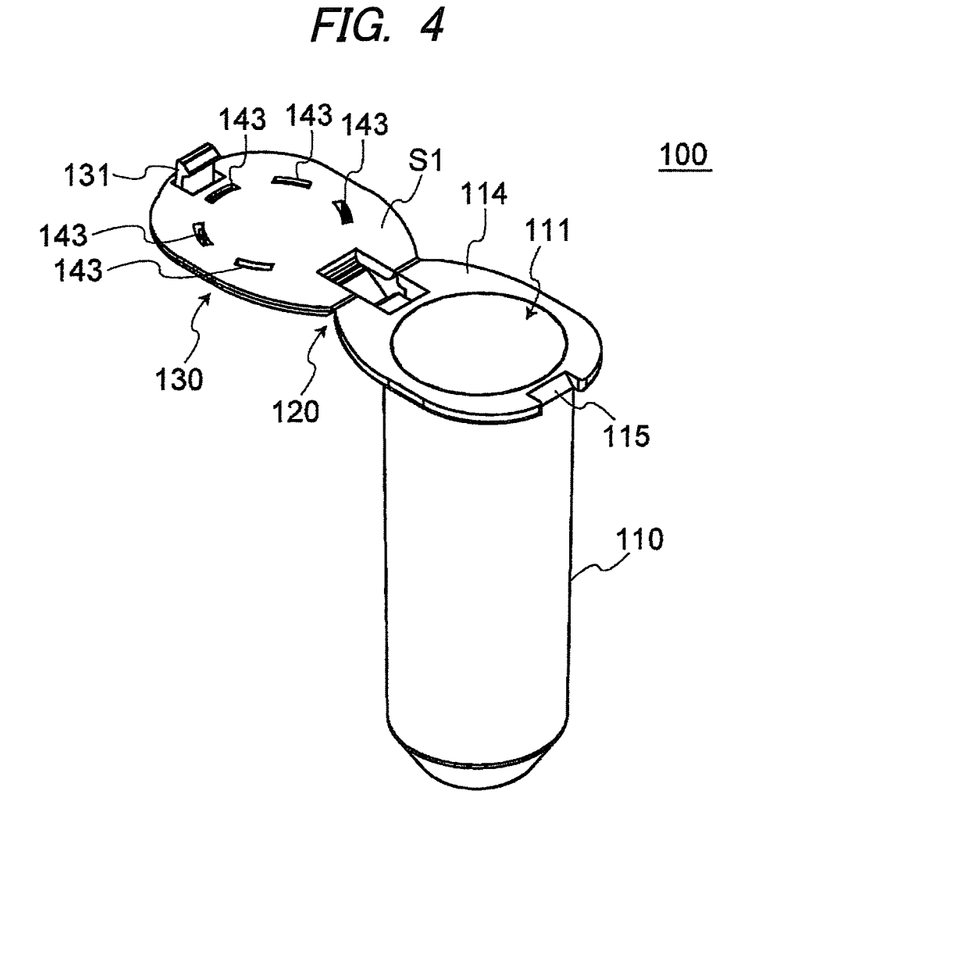
FIG. 4 is a perspective view of a sampling holder 100, which is taken from the direction of an opening portion 111.
Figure 5:
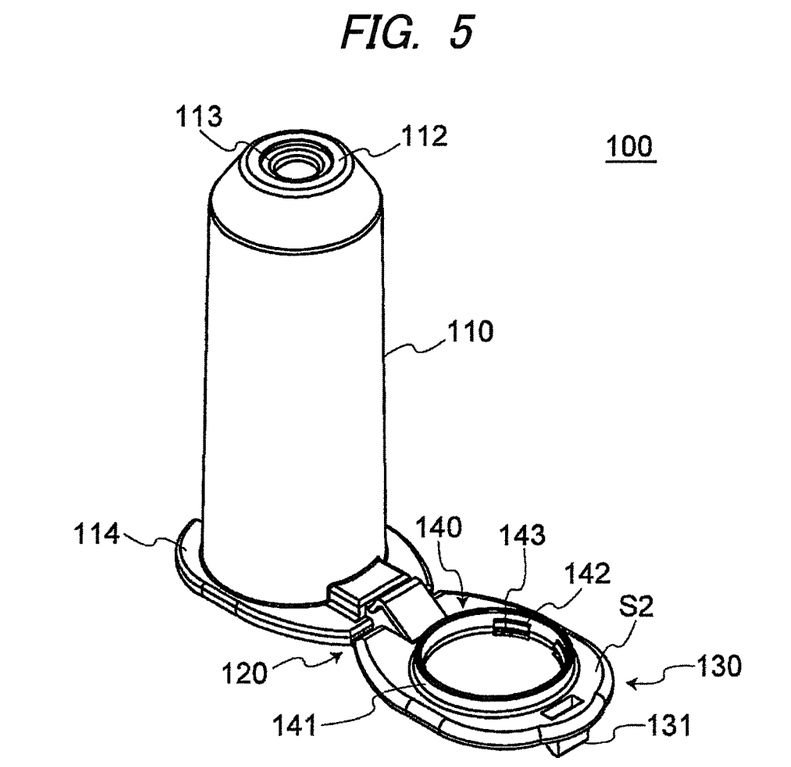
FIG. 5 is a perspective view of the sampling holder 100, which is taken from the direction of a needle mounting portion 113.

FIG. 4 is a perspective view of the sampling holder 100 taken from the direction of an opening portion 111. FIG. 5 is a perspective view of the sampling holder 100 taken from the direction of a needle mounting portion 113.

As illustrated in FIGS. 4 and 5, the sampling holder 100 according to the embodiment includes a tubular body 110 opened at both sides, the lid 130 capable of opening and closing one of the opening portions 111 of the tubular body 110, and the fitting portion 140 provided on a front-surface S2 of the lid 130. For example, plastic materials, such as polypropylene, can preferably be used as the material of the sampling holder 100.

The tubular body 110 has a cylindrical shape and is provided with the opening portion 111 at one end thereof. The other end portion at the side of the needle mounting portion 113, i.e., the other end portion of the tubular body 110 has a tapered shape whose diameter is reduced. The leading end having a tapered shape includes a circular surface 112 formed to be substantially perpendicular to the central axis of the tubular body 110. The center of the circular surface 112 is opened. This opening is provided with the needle mounting portion 113. A blood collection tube sampling needle 440 (see FIG. 1) is mounted in the needle mounting portion 113.

An opening flange portion 114 having a substantially elliptical shape is provided on the edge of the opening portion 111 of the tubular body 110. A click engaging portion 115 is provided in the opening flange portion 114 and formed to be engageable with a click portion 131 of the lid 130.

In addition, a hinge 120 is provided opposite to the click engaging portion 115 of the opening flange portion 114. The lid 130 is connected thereto via the hinge 120.

The lid 130 has the substantially same shape as that of the outer circumferential shape of the opening flange portion 114, i.e., has a substantially elliptical shape.

The click portion 131 is provided on a back-surface S1 of the lid 130 at a given position (i.e., the position opposite to the hinge 120). The leading end of the click portion 131 is formed to protrude like a hook toward the hinge 120 and to be engageable with the click engaging portion 115 when the lid 130 is closed.

Figure 6A:
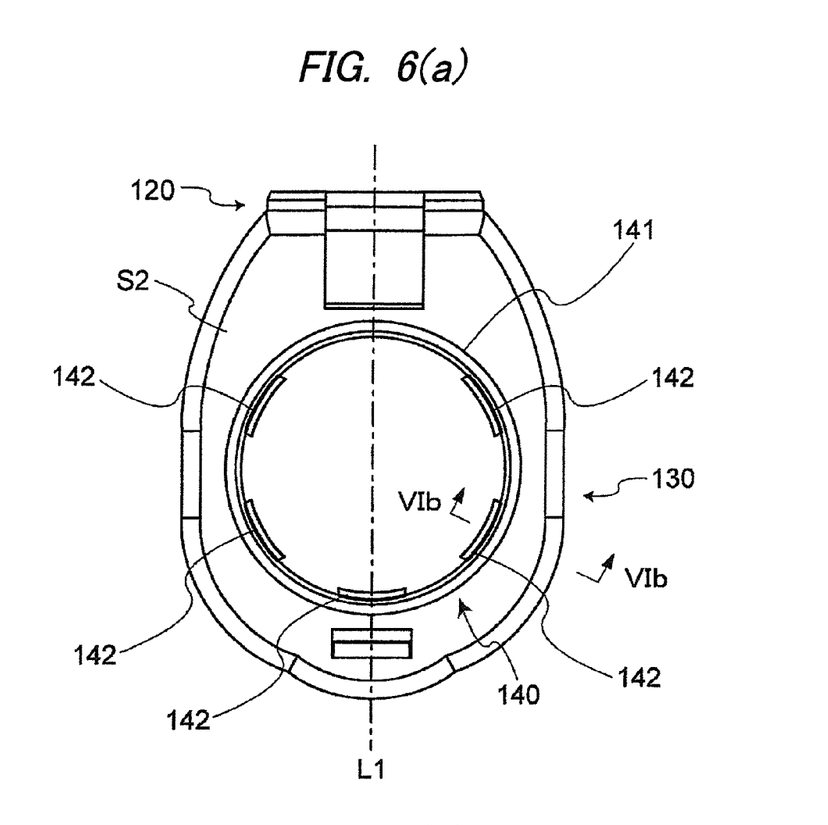
FIG. 6(a) is a view of a lid 130 taken from the direction of a lid front-surface S2.
Figure 6B:
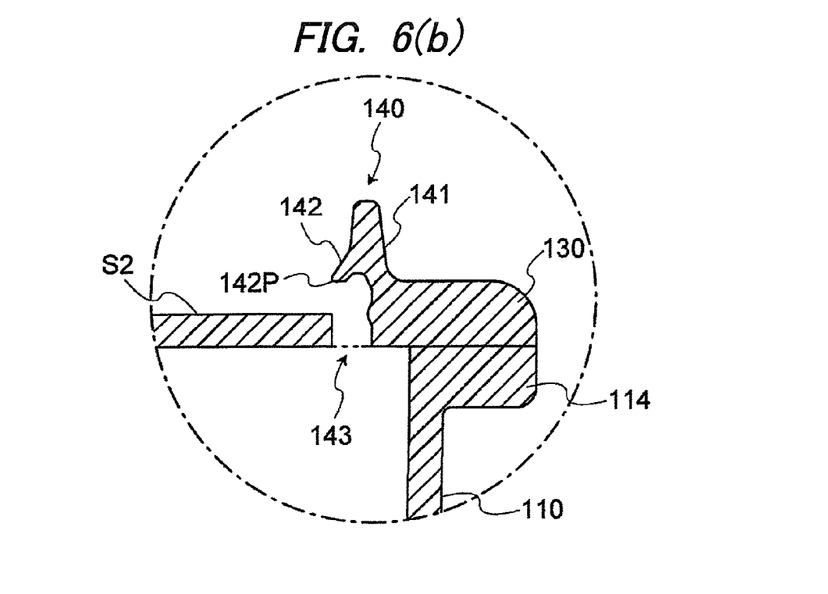
FIG. 6(b) is an end view taken in the direction of arrows VIb-VIb shown in FIG. 6 (a).

FIGS. 6(a) and 6(b) are views illustrating the fitting portion 140 of the sampling holder 100, in which FIG. 6(a) is a view of the lid 130 taken from the direction of the lid front-surface S2, and FIG. 6(b) is a partial end view of the periphery of each catching portion 142 (i.e., an end view taken in the direction of arrows VIb-VIb shown in FIG. 6(a)).

The fitting portion 140 includes a circumferential rib 141 serving as a rib portion, and each catching portion 142 including a protrusion provided on the inner circumferential surface of the circumferential rib 141. The circumferential rib 141 is formed to be positioned such that the circumference of the circumferential rib 141 overlaps with that of the opening portion 111 of the tubular body 110 when the lid 130 is closed. That is, the central axis of the circumferential rib 141 substantially coincides with that of the opening portion 111. The diameter of the circumferential rib 141 is substantially equal to that of the opening portion 111. The circumferential rib 141 is formed so that a protrusion height of the circumferential rib 141 (the height of the circumferential rib 141 protruding from the lid front-surface S2) is, e.g., about 2 mm.

Each catching portion 142 including a protrusion is formed to protrude from the inner circumferential surface of the circumferential rib 141 toward the central axis thereof. For example, five catching portions 142 are provided to be arranged symmetrically with respect to an imaginary line L1 perpendicular to the central axis of the circumferential rib 141 (see FIG. 6(a)). The distal end 142P of each catching portion 142 extends toward the lid front-surface S2. An outer side surface of each catching portion 142 is formed as an inclined surface (see FIG. 6(b)).

As illustrated in FIG. 1, the sampling holder 100 is used by connecting, to the sampling bag 320, the needle mounting portion 113 in which the sampling needle 440 is installed.

When blood is pooled in the sampling bag 320, a worker opens the lid 130, and inserts a blood collection tube (not shown) into the tubular body 110. Thus, the worker collects the blood pooled in the sampling bag 320. After the blood collection, the worker pulls the blood collection tube out of the tubular body 110 and closes the tubular body 110 with the lid 130.

Figure 7A:
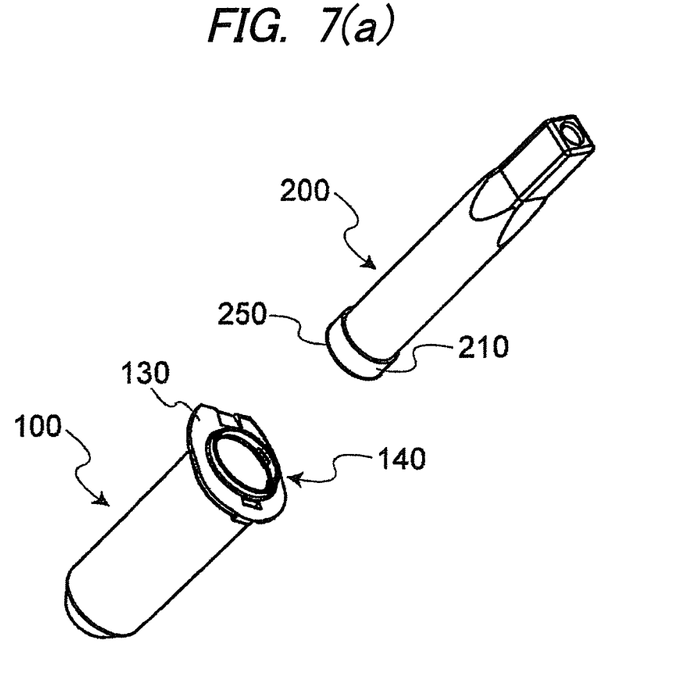
FIG. 7(a) is a view taken before the needlestick-preventive needle cover 200 is fit into the sampling holder 100.
Figure 7B:
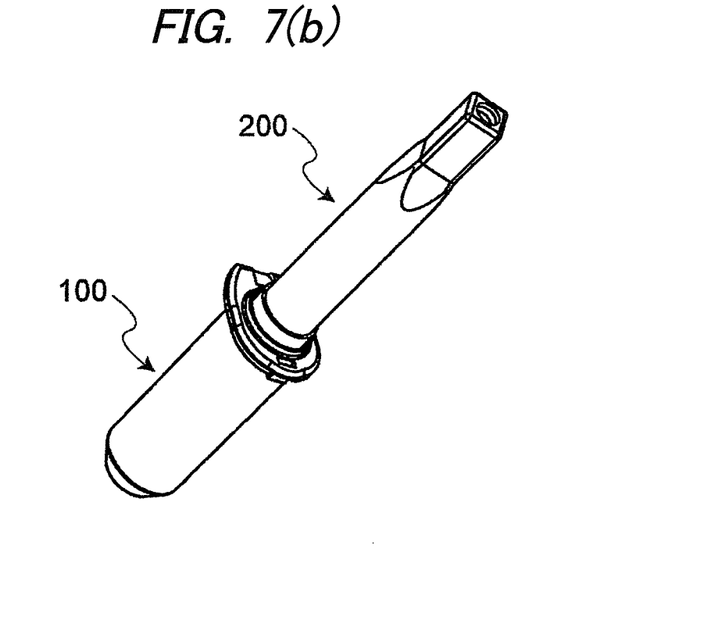
FIG. 7(b) is a view taken when the needlestick-preventive needle cover 200 is fit into the sampling holder 100.

FIGS. 7(a) and 7(b) are views illustrating the fitting between the needlestick-preventive needle cover 200 and the sampling holder 100, in which FIG. 7(a) is a view taken before the needlestick-preventive needle cover 200 is fit into the sampling holder 100, and FIG. 7(b) is a view taken when the needlestick-preventive needle cover 200 is fit into the sampling holder 100.

Figure 8A:
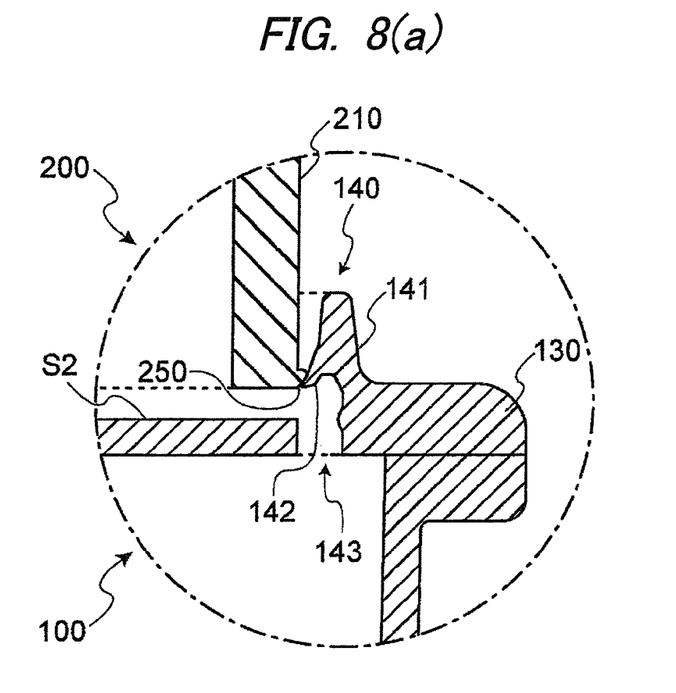
FIG. 8(a) is a partial end view illustrating a state in which each engaging portion 250 touches an associated catching portion 142.
Figure 8B:
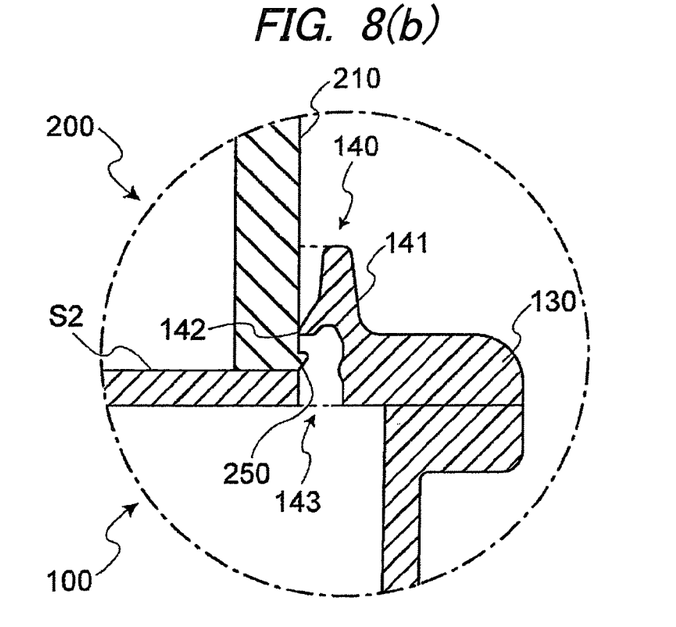
FIG. 8(b) is a partial end view illustrating a state in which each engaging portion 250 has ridden over an associated catching portion 142.

In addition, FIGS. 8(a) and 8(b) are views illustrating the relationship between each catching portion 142 and an engaging portion 250 at the fitting therebetween, in which FIG. 8(a) is a partial end view illustrating a state in which the engaging portion 250 touches each catching portion 142, and FIG. 8(b) is a partial end view illustrating a state in which the engaging portion 250 has ridden over each catching portion 142.

When the needlestick-preventive needle cover 200 that accommodates the blood collection needle 410 is fit into the sampling holder 100, the needlestick-preventive needle cover 200 is moved closer to the lid 130 in a state in which the tubular body 110 is closed with the lid 130, as illustrated in FIG. 7(a). Then, the tubular body flange portion 210 is inserted into the fitting portion 140 of the lid 130, so that the sampling holder 100 and the needlestick-preventive needle cover 200 engage with each other, as illustrated in FIG. 7(b).

At that time, the engaging portion 250 touches and is pressed by the catching portion 142, as illustrated in FIG. 8(a). Thus, the engaging portion 250 is inserted thereinto by causing a side surface of the engaging portion 250 to move along an inclined surface of the catching portion 142. The fitting therebetween is completed by causing the engaging portion 250 to ride over each catching portion 142, as illustrated in FIG. 8(b). When the engaging portion 250 rides over each catching portion 142, a click-sound is generated. Thus, the worker can determine that the fitting therebetween is completed.

In the lid 130 of the sampling holder 100, holes 143 are provided in the boundary part between the lid front surface S2 and the circumferential rib 141. As seen from FIGS. 4 and 6, the holes 143 are provided at positions corresponding to the catching portion 142.

The blood collection set 500 according to the embodiment of the configuration is such that when the needlestick-preventive needle cover 200 is fit into the fitting portion 140, each catching portion 142 engages with the engaging portion 250. Thus, the sampling holder 100 and the needlestick-preventive needle cover 200 can be made by an engaging force therebetween to be considerably more difficult to disengage from each other than conventional.

In addition, the blood collection set 500 according to the embodiment is such that the needlestick-preventive needle cover 200 is fit into the fitting portion 140 of the sampling holder 100 by causing the catching portion to catch the engaging portion 250. Thus, the blood collection set 500 according to the embodiment can fit the needlestick-preventive needle cover 200 into the fitting portion 140 by a smaller force, as compared with the case of the conventional blood collection set in which the needlestick-preventive needle cover is pressed into the fitting portion of the lid.

In the blood collection set 500 according to the embodiment, each catching portion 142 includes a plurality of protrusions. Thus, the blood collection set 500 is such that the sampling holder 100 and the needlestick-preventive needle cover 200 are more difficult to disengage from each other.

In the blood collection set 500 according to the embodiment, as illustrated in FIG. 6(a), the plurality of protrusions (the catching portion 142) are arranged symmetrically with respect to the imaginary line L1 perpendicular to the central axis of the circumferential rib 141. Thus, the protrusions (the catching portions 142) are arranged in a balanced manner, so that there is no imbalance in locations where the needlestick-preventive needle cover 200 is caught. Accordingly, the blood collection set is such that the sampling holder 100 and the needlestick-preventive needle cover 200 are difficult to disengage from each other, and easily fit to each other.

In the blood collection set 500 according to the embodiment, the catching portion 142 includes the protrusions. The holes 143 are provided at the positions corresponding to the catching portions 142 in the boundary portion between the lid front-surface S2 and the circumferential rib 141.

While fitting the needlestick-preventive needle cover 200 into the fitting portion 140, when the engaging portion 250 of the needlestick-preventive needle cover 200 presses the catching portion 142, a resistance force resisting the pressing acts upon the catching portion 142. At that time, the resistance force acting upon the catching portion 142 can be reduced to a relatively small value. Consequently, the resistance at the time of fitting the needlestick-preventive needle cover 200 into the fitting portion 140 can be reduced to a small value. Thus, the needlestick-preventive needle cover 200 can be fit into the fitting portion 140 by smaller force.

In the blood collection set 500 according to the embodiment, the lid 130 is connected to the tubular body 110 via the hinge 120. Thus, the lid 130 is never lost when the lid 130 is uncapped.

In the blood collection set 500 according to the embodiment, the click portion 131 is provided at an end portion of the lid 130. The click engaging portion 115 engaging with the click portion 131 is provided in the vicinity of the opening portion 111 of the tubular element 110. Thus, the opening portion 111 of the tubular body 110 can relatively easily be closed by the lid 130.

In the blood collection set 500 according to the embodiment, the catching portion 142 includes the protrusions. Each distal end 142P of the catching portion 142 extends toward the lid front-surface S2 (see FIG. 6(b)). That is, each catching portion 142 is a so-called "barb".

Thus, after the engaging portion 250 rides over each catching portion 142 (when the fitting of the needlestick-preventive needle cover 200 is completed), the engaging portion 250 and the catching portion 142 surely engage with each other even when the needlestick-preventive needle cover 200 moves in a direction opposite to the lid front-surface S2 (the direction in which the needlestick-preventive needle cover 200 disengage). Thus, the needlestick-preventive needle cover 200 can be more restrained from being disengaged from the fitting portion 140.

In the blood collection set 500 according to the embodiment, the protrusion height of the circumferential rib 141 serving as a rib portion ranges from 1 mm to 5 mm.

If the protrusion height of the circumferential rib 141 is less than 1 mm, the catching portion 142 is relatively small. Accordingly, it is not easy to obtain an engaging force of a desirable level.

On the other hand, if the protrusion height of the circumferential rib 141 is higher than 5 mm, it may be difficult to demold the sampling holder 100 from a mold at the time of manufacture thereof.

Therefore, the protrusion height of the circumferential rib 141 serving as a rib portion is set to range from 1 mm to 5 mm. Thus, it is difficult to disengage from each other, and the blood collection set is easy to manufacture.

The sampling holder 100 according to the embodiment includes the catching portion 142. Thus, for a reason similar to that in the case of the blood collection set 500, the sampling holder 100 is such that when the needlestick-preventive needle cover 200 is fit thereinto, the needlestick-preventive needle cover 200 is difficult to disengage therefrom, as compared with the case of being fit into the conventional sampling holder, and that the needlestick-preventive needle cover 200 can be fit thereinto by a force smaller than that needed in the case of being fit into the conventional sampling holder.

The needlestick-preventive needle cover 200 according to the embodiment includes the engaging portion 250. Thus, for a reason similar to that in the case of the blood collection set 500, the needlestick-preventive needle cover 200 is such that when fit into the sampling holder 100, the needlestick-preventive needle cover 200 is difficult to disengage from the sampling holder 100 than conventional, and that the needlestick-preventive needle cover 200 can be fit into the fitting portion 140 of the sampling holder 100 by force smaller than conventional.

The embodiment described hereinabove only exemplifies a specific example of the present invention. The scope of the invention is not limited to the embodiment but can include various modifications within the scope of the technical ideas thereof.

(1) According to the embodiment, the blood collection set 500 includes a plurality of bags (the blood bag 310, the sampling bag 320, the first bag 330, the second bag 340, and the blood storage solution containing bag 350). However, the present invention is not limited thereto. The types of the bag are not limited to the bags described above. The number of bags can be 1 to 4 or can be 6 or more. In addition, according to the embodiment, the blood collection set 500 includes the blood filter 450. However, the blood filter is not indispensable.

That is, as long as the blood collection set includes at least the needlestick-preventive needle cover and the sampling holder, the configuration of the blood collection set is not limited to a specific one.

(2) In the embodiment, both of each catching portion 142 of the sampling holder 100 and the engaging portion 250 of the needlestick-preventive needle cover 200 are the protrusions. However, the catching portion and the engaging portion according to the invention are not limited thereto. One of the catching portion and the engaging portion can be a recess. That is, the catching portion and the engaging portion can be the combination of the catching portion formed of a protrusion, and the engaging portion formed of a recess, or that of the catching portion formed of a recess, and the engaging portion formed of a protrusion.

(3) According to the embodiment, the catching portion 142 of the sampling holder 100 is a protrusion protruded from the inner circumferential surface of the circumferential rib 141 serving as a rib portion. The catching portion according to the invention is not limited thereto. The catching portion can be a protrusion or a recess, which is provided on the outer circumferential surface of a rib portion. In this case, it is recommendable to set the tubular body flange portion 210 of the needlestick-preventive needle cover 200 such that the inner circumferential surface of the tubular body flange portion 210 is placed at an outer side than the outer circumferential surface of the rib portion, and that the engaging portion is formed on an edge portion of the inner circumferential surface of the tubular body flange portion 210. Although the embodiment has been described by exemplifying a case in which the outer circumferential surface of the tubular body flange portion 210 is set to be placed at an inner side than the inner circumferential surface of the fitting portion 140, the invention is not limited to this case. Incidentally, if the catching portion and the engaging portion engage each other, the inner circumferential surface of the tubular body flange portion 210 and the outer circumferential surface of the rib portion, or the outer circumferential surface of the tubular body flange portion 210 and the inner circumferential surface of the rib portion can be either contacted with each other or separated from each other. For example, if one of the catching portion and the engaging portion is a protrusion or the other of the catching portion and the engaging portion is a recess, the inner circumferential surface or the outer circumferential surface of the tubular body flange portion 210 can be configured to be contacted with the outer circumferential surface or the inner circumferential surface of the rib portion.

(4) The embodiment has exemplified a case where there are five catching portions 142 of the sampling holder 100. However, the invention is not limited to this case. The number of the catching portions can be 1 to 4 or can be 6 or more.

(5) In the embodiment, the tubular body 110 of the sampling holder 100 is connected to the lid 130 via the hinge 120. However, the invention is not limited to this configuration. A connection portion therebetween can be, e.g., a cord-like member or a chain-like member other than the hinge.

The tubular body 110 and the lid 130 can be separated from each other via nothing. In this case, the tubular body and the lid can differ in material from each other.

(6) In the embodiment, an end portion of the sampling holder 100, which is at the side of the needle mounting portion 113, has a tapered shape. The invention is not limited to this configuration. This end portion can have a shape other than the tapered shape.

(7) In the embodiment, the tubular body 110 of the sampling holder 100 is cylindrically-shaped. However, the tubular body of the invention is not limited thereto. The tubular body can be polygonally-shaped, as long as a blood collection tube can be inserted thereinto.

(8) The embodiment has been described by exemplifying the circumferential rib 141 as the rib portion. However, the rib portion according to the invention is not limited thereto. The rib portion can have a polygonal shape, such as a triangle and a rectangle, other than a circular-shape. In addition, a rib configuring the rib portion is not necessarily shaped to be entirely continuous. The rib can have a partially cut-out shape.

(9) In the embodiment, the needlestick-preventive needle cover 200 is configured by the tubular body including the large-diameter portion 220 that is circularly cross-sectionally shaped, and the polygonal portion 240 that is substantially square shaped. The invention is not limited to this tubular body. The tubular body according to the invention can be either that having a circular cross-section as a whole, or that having a polygonal cross-section as a whole.

In addition, in the embodiment, the polygonal portion 240 of the needlestick-preventive needle cover 200 has a substantially square cross-section. The invention is not limited to this polygonal portion. The shape of the polygonal portion can substantially be a triangle or a polygon with five or more sides.

As long as the blood election tube and the blood collection needle can be inserted into the tubular body, the shape of a cross-section of the tubular body of the needlestick-preventive needle cover is not limited to a specific one.

(10) In the embodiment, the engaging portion 250 of the needlestick-preventive needle cover 200 is provided to protrude outwardly over the entire circumference thereof. However, the invention is not limited to this engaging portion. The engaging portion 250 is not necessarily shaped to be entirely continuous. The engaging portion 250 can have a partially cut-out shape.

(11) Apparently, the sampling holder and the needlestick-preventive needle cover can be applied not only to a blood collection set having a bag for collecting and preserving blood or the like but to a transfusion circuit set or the like configured to be connectable to a transfusion bag for infusion or to a blood circuit set used for hemodialysis.

This application is based on Japanese Patent Application No. 2009-156592 filed on Jul. 1, 2009, the content of which is incorporated herein by reference.

INDUSTRIAL APPLICABILITY

The blood collection set having the sampling holder and the needlestick-preventive needle cover according to the invention can surely engage the sampling holder and the needlestick-preventive needle cover. Thus, the disposal of needles used in the medical field can safely and reliably be performed. The blood collection set according to the invention can be utilized not only for a blood collection set having a blood collection needle but for a blood circuit set having a dialysis needle, a transfusion circuit set having an infusion needle, and the like.

EXPLANATION OF REFERENCE NUMERALS AND SIGNS 100 sampling holder
110 tubular body
111 opening portion
112 circular surface
113 needle mounting portion
114 opening flange portion
115 click engaging portion
120 hinge
130 lid
131 click portion
140 fitting portion
141 circumferential rib
142 catching portion
142P distal end of the catching portion
143 hole
200 needlestick-preventive needle cover
210 tubular body flange portion
220 large-diameter portion
240 polygonal portion
250 engaging portion
260 tube insertion path
310 blood bag
320 sampling bag
330 first bag
340 second bag
350 blood storage solution containing bag
410 blood collection needle
420 first branching tube
430 second branching tube
440 sampling needle
450 blood filter
500 blood collection set
L1 imaginary line perpendicular to the central axis of the circumferential rib
S1 lid back-surface
S2 lid front-surface
T1 blood collection tube
T2 initial blood flow introduction tube
T3 first connection tube
T4 second connection tube
T5 third connection tube
T6 fourth connection tube

The invention claimed is:
1. A blood collection set comprising:
a sampling holder comprising a tubular body having an opening portion, a lid configured to open and close the opening portion of the tubular body, and a fitting portion provided on a surface of the lid on a side of the lid that is opposite to the tubular body; and
a tubular needlestick-preventive needle cover configured to fit into the fitting portion, wherein the tubular needlestick-preventive needle cover is opened at both ends, and configured to accommodate a blood collection needle therein,
wherein the fitting portion comprises:
a rib portion protruding from the surface of the lid that is opposite to the tubular body;
a catching portion comprising at least one protrusion provided on the rib portion, wherein the tubular needlestick-preventive needle cover comprises an engaging portion configured to engage with the catching portion, and the fitting portion further comprises at least one hole provided in a boundary portion between the rib portion and the surface of the lid on the side opposite to the tubular body and at a position directly adjacent to the at least one protrusion, wherein the at least one protrusion comprises a plurality of protrusions and the at least one hole comprises a plurality of holes corresponding to the plurality of protrusions.

2. The blood collection set according to claim 1, wherein the rib portion comprises a circumferential rib, and the plurality of protrusions are arranged symmetrically with respect to an imaginary line perpendicular to a central axis of the circumferential rib.

3. The blood collection set according to claim 1, wherein a distal end of the catching portion extends toward a surface of the lid on a side of the tubular body.

4. The blood collection set according to claim 1, wherein a click portion is provided on an end portion of the lid; and a click engaging portion engaging with the click portion is provided near the opening portion of the tubular body.

5. A sampling holder comprising:

a tubular body comprising an opening portion, a lid configured to open and close the opening portion of the tubular body, a hinge via which the lid is connected to the tubular body, and a fitting portion provided on a surface of the lid on a side of the lid that is opposite to the tubular body, wherein the fitting portion comprises:

a rib portion protruding from the surface of the lid that is opposite to the tubular body; and a catching portion comprising at least one protrusion provided on the rib portion and at least one hole provided in a boundary portion the rib portion and the surface of the lid on the side opposite to the tubular body and at a position directly adjacent to the at least one protrusion, wherein a central portion of the surface of the lid that is opposite to the tubular body is a flat planar surface configured to close the opening of the tubular body, wherein the at least one protrusion comprises a plurality of protrusions and the at least one hole comprises a plurality of holes corresponding to the plurality of protrusions.

6. The blood collection set according to claim 1, wherein sampling holder further comprises a hinge via which the lid is connected to the tubular body.

* * * * *